United States Patent
Harris, III et al.

(10) Patent No.: US 7,576,103 B2
(45) Date of Patent: *Aug. 18, 2009

(54) TETRALIN AND INDANE DERIVATIVES AND USES THEREOF

(75) Inventors: Ralph New Harris, III, Redwood City, CA (US); Nancy Elisabeth Krauss, Mountain View, CA (US); James M. Kress, Sanford, NC (US); David Bruce Repke, Milpitas, CA (US); Russell Stephen Stabler, Boulder Creek, CA (US)

(73) Assignee: Roche Palo Alto LLC, Palo Alto, CA (US)

(*) Notice: Subject to any disclaimer, the term of this patent is extended or adjusted under 35 U.S.C. 154(b) by 611 days.

This patent is subject to a terminal disclaimer.

(21) Appl. No.: 11/316,003

(22) Filed: Dec. 21, 2005

(65) Prior Publication Data

US 2006/0154965 A1    Jul. 13, 2006

Related U.S. Application Data

(60) Provisional application No. 60/638,031, filed on Dec. 21, 2004.

(51) Int. Cl.
*A61K 31/445* (2006.01)
*C07D 211/06* (2006.01)

(52) U.S. Cl. .......... 514/319; 514/359; 514/613; 514/651; 546/205; 546/206; 564/86; 564/147; 564/338

(58) Field of Classification Search .......... 514/319, 514/359, 613, 651; 546/205, 206; 564/86, 564/147, 338
See application file for complete search history.

(56) References Cited

U.S. PATENT DOCUMENTS

| | | | |
|---|---|---|---|
| 5,137,901 A | 8/1992 | Junge et al. | |
| 5,374,643 A | 12/1994 | Atwal et al. | |
| 5,412,117 A | 5/1995 | Koga et al. | |
| 5,614,633 A | 3/1997 | Koga et al. | |
| 5,627,138 A | 5/1997 | Anderson et al. | |
| 5,646,308 A | 7/1997 | Koga et al. | |
| 5,663,194 A | 9/1997 | Mewshaw | |
| 5,719,182 A | 2/1998 | Cousins et al. | |
| 5,739,135 A | 4/1998 | Biller et al. | |
| 5,817,693 A | 10/1998 | Cousins et al. | |
| 5,869,478 A | 2/1999 | Ding et al. | |
| 5,874,446 A | 2/1999 | Koga et al. | |
| 5,883,099 A | 3/1999 | Biller et al. | |
| 5,935,958 A | 8/1999 | Kozlowski et al. | |
| 5,977,167 A | 11/1999 | Koga et al. | |
| 6,083,982 A | 7/2000 | Wechter et al. | |
| 6,150,402 A | 11/2000 | Wechter et al. | |
| 6,214,881 B1 | 4/2001 | Xiang | |
| 6,448,243 B1 | 9/2002 | Kitazawa et al. | |
| 6,479,536 B1 | 11/2002 | Ohkawa et al. | |
| 6,559,144 B2 | 5/2003 | Diefenbach et al. | |
| 6,605,632 B1 | 8/2003 | Lesieur et al. | |
| 6,613,805 B2 | 9/2003 | Kato et al. | |
| 6,638,972 B2 | 10/2003 | Kelly et al. | |
| 6,660,752 B2 | 12/2003 | O'Connor et al. | |
| 6,706,757 B2 | 3/2004 | Greenblatt et al. | |
| 6,784,314 B2 | 8/2004 | Yamashita et al. | |
| 7,312,359 B2 * | 12/2007 | Greenhouse et al. | ........ 564/147 |
| 2002/0002177 A1 | 1/2002 | Cousins et al. | |
| 2004/0024210 A1 | 2/2004 | Johansson et al. | |
| 2004/0087577 A1 | 5/2004 | Pratt et al. | |
| 2004/0097492 A1 | 5/2004 | Pratt et al. | |
| 2004/0162285 A1 | 8/2004 | Pratt et al. | |
| 2004/0167123 A1 | 8/2004 | Pratt et al. | |
| 2005/0075331 A1 | 4/2005 | Pratt et al. | |
| 2005/0154053 A1 | 7/2005 | Rhijn et al. | |
| 2008/0015256 A1* | 1/2008 | Harris et al. | ................ 514/605 |

FOREIGN PATENT DOCUMENTS

| | | |
|---|---|---|
| EP | 0 488 616 A1 | 6/1992 |
| EP | 0 587 180 A2 | 9/1992 |
| EP | 1 088 819 A2 | 4/2001 |
| EP | 0 747 374 B1 | 12/2001 |
| JP | 10 195056 A | 7/1998 |
| WO | WO 93/08799 A1 | 5/1993 |
| WO | WO 94/25013 A1 | 11/1994 |
| WO | WO 97/02259 A1 | 1/1997 |
| WO | WO 98/07418 A1 | 2/1998 |
| WO | WO 98/38156 A1 | 9/1998 |
| WO | WO 01/85172 A2 | 11/2001 |
| WO | WO 01/87293 A1 | 11/2001 |
| WO | WO 02/18335 A1 | 3/2002 |

(Continued)

OTHER PUBLICATIONS

Fong et al. "1,2,3,4-tetrahydrocarbazoles . . . " Bioorg. Med. Chem. Let. 14 p. 1961-1964 (2004).*

(Continued)

*Primary Examiner*—Celia Chang
(74) *Attorney, Agent, or Firm*—Robert C. Hall

(57) ABSTRACT

Compounds of the formula I:

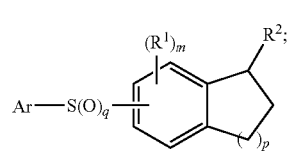

or pharmaceutically acceptable salts thereof,
wherein m, p, q, Ar, $R^1$ and $R^2$ are as defined herein. Also provided are methods for preparing, compositions comprising, and methods for using compounds of formula I.

30 Claims, No Drawings

FOREIGN PATENT DOCUMENTS

| WO | WO 02/098424 A1 | 12/2002 |
| WO | WO 03/037262 A2 | 5/2003 |
| WO | WO 03/059356 A2 | 7/2003 |
| WO | WO 03/099801 A1 | 12/2003 |
| WO | WO 2004/052312 A2 | 6/2004 |
| WO | WO 2004/052313 A2 | 6/2004 |
| WO | WO 2004/058150 A2 | 7/2004 |
| WO | WO 2005/019191 A2 | 3/2005 |
| WO | WO 2005/040355 A2 | 5/2005 |

OTHER PUBLICATIONS

Pullagurla et al. "N-benzenesulfonylgramine . . . " Bioorg. Med. Chem. Let. 13 p. 3355-3399 (2003).*

Rubini et al. Synthesis of isosteric . . . Tetrahedron. v.42, p. 6039-6045 (1986).*

Patani et al. "bioisosterism: a rational . . . " Chem. Rve. v.96, p. 3147, 3169-3171 (1996).*

Dhanak, D. et. al. "Identification and Biological Characterization of Heterocyclic Inhibitors of the Hepatitis C Virus RNA-dependent RNA Polymerase," *J. Biological Chem.* vol. 277, No. 41 (2002) pp. 38322-38327.

Gu, B. et. al., "Arresting Initiation of Hepatitis C Virus RNA Synthesis Using Heterocyclic Derivatives," *J. Biological Chem.*, vol. 278, No. 19 (2003) pp. 16602-16607.

Nguyen, T. T. et. al., "Resistance Profile of a Hepatitis C Virus RNA-Dependent RNA Polymerase Benzothiadiazine Inhibitors," *American Soc. Microbiology*, vol. 47, No. 11 (2003) pp. 3525-3530.

* cited by examiner

TETRALIN AND INDANE DERIVATIVES AND USES THEREOF

CROSS REFERENCE TO RELATED APPLICATIONS

This application claims the benefit of priority of U.S. Provisional Patent Application Ser. No. 60/638,031 filed Dec. 21, 2004, the disclosure of which is incorporated herein by reference in its entirety.

FIELD OF THE INVENTION

This invention relates to substituted indane and tetralin compounds, and associated compositions, methods for use as therapeutic agents, and methods of preparation thereof.

BACKGROUND OF THE INVENTION

The actions of 5-hydroxytryptamine (5-HT) as a major modulatory neurotransmitter in the brain are mediated through a number of receptor families termed 5-HT1, 5-HT2, 5-HT3, 5-HT4, 5-HT5, 5-HT6, and 5-HT7. Based on a high level of 5-HT6 receptor mRNA in the brain, it has been stated that the 5-HT6 receptor may play a role in the pathology and treatment of central nerve system disorders. In particular, 5-HT2-selective and 5-HT6 selective ligands have been identified as potentially useful in the treatment of certain CNS disorders such as Parkinson's disease, Huntington's disease, anxiety, depression, manic depression, psychoses, epilepsy, obsessive compulsive disorders, mood disorders, migraine, Alzheimer's disease (enhancement of cognitive memory), sleep disorders, feeding disorders such as anorexia, bulimia and obesity, panic attacks, akathisia, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such compounds are also expected to be of use in the treatment of certain gastrointestinal (GI) disorders such as functional bowel disorder. See for example, B. L. Roth et al., J. Pharmacol. Exp. Ther., 1994, 268, pages 1403-14120, D. R. Sibley et al., Mol. Pharmacol., 1993, 43, 320-327, A. J. Sleight et al., Neurotransmission, 1995, 11, 1-5, and A. J. Sleight et al., Serotonin ID Research Alert, 1997, 2(3), 115-8.

While some 5-HT6 and 5-HT2A modulators have been disclosed, there continues to be a need for compounds that are useful for modulating the 5-HT6 receptor, the 5-HT2A receptor, or both.

SUMMARY

The invention provides compounds of the formula I:

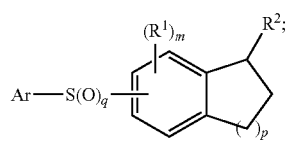

or a pharmaceutically acceptable salt thereof, wherein:
m is from 0 to 3;
p is from 1 to 3;
q is 0, 1 or 2;
Ar is optionally substituted aryl or optionally substituted heteroaryl;
each $R^1$ is independently halo, alkyl, haloalkyl, heteroalkyl, cyano, $-S(O)_q-R^a$, $-C(=O)-NR^bR^c$, $-SO_2-NR^bR^c$, $-N(R^d)-C(=O)-R^e$, or $-C(=O)-R^e$, where q is from 0 to 2, $R^a$, $R^b$, $R^c$, $R^d$ and $R^e$ each independently is hydrogen or alkyl;

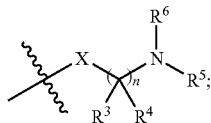

$R^2$ is
X is $-O-$ or $-NR^7-$;
n is 2 or 3;
$R^3$ and $R^4$ each independently is hydrogen or alkyl, or $R^3$ and $R^4$ together may form a $-C(O)-$;
$R^5$ and $R^6$ each independently is hydrogen or alkyl, or $R^5$ and $R^6$ together with the nitrogen to which they are attached may form a five- or six-membered ring that optionally includes an additional heteroatom selected from O, N and S, or one of $R^5$ and $R^6$ and one of $R^3$ and $R^4$ together with the atoms to which they are attached may form a five- or six-membered ring that optionally includes an additional heteroatom selected from O, N and S; and
$R^7$ is hydrogen or alkyl.

The invention also provides methods for preparing, methods of using, and pharmaceutical compositions comprising the aforementioned compounds.

DETAILED DESCRIPTION OF THE INVENTION

The invention provides substituted quinolinone compounds, associated compositions, methods for use as therapeutic agents, and methods of preparation thereof. In specific embodiments the invention provides piperazinyl-substituted quinolinone compounds and associated pharmaceutical compositions, and methods for using the same in the treatment of central nervous system (CNS) diseases and gastrointestinal tract disorders.

All publications cited in this disclosure are incorporated herein by reference in their entirety.

DEFINITIONS

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Agonist" refers to a compound that enhances the activity of another compound or receptor site.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms (i.e., "$C_1$-$C_6$alkyl"). Examples of alkyl groups include, but are not limited to, methyl, ethyl, propyl, isopropyl, isobutyl, sec-butyl, tert-butyl, pentyl, n-hexyl, octyl, dodecyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkenylene" means a linear unsaturated divalent hydrocarbon radical of two to six carbon atoms or a branched saturated divalent hydrocarbon radical of three to six carbon atoms, e.g., ethenylene (—CH═CH—), 2,2-dimethylethenylene, propenylene, 2-methylpropenylene, butenylene, pentenylene, and the like.

"Alkoxy" means a group —OR, wherein R is alkyl as defined herein. Examples of alkoxy moieties include, but are not limited to, methoxy, ethoxy, isopropoxy, and the like.

"Aminoalkyl" means a group —R—R' wherein R' is amino and R is alkylene as defined herein. "Aminoalkyl" includes aminomethyl, aminoethyl, 1-aminopropyl, 2-aminopropyl, and the like. The amino moiety of "aminoalkyl" may be substituted once or twice with alkyl to provide "alkylaminoalkyl" and "dialkylaminoalkyl" respectively. "Alkylaminoalkyl" includes methylaminomethyl, methylaminoethyl, methylaminopropyl, ethylaminoethyl and the like. "Dialkylaminoalkyl" includes dimethylaminomethyl, dimethylaminoethyl, dimethylaminopropyl, N-methyl-N-ethylaminoethyl, and the like.

"Antagonist" refers to a compound that diminishes or prevents the action of another compound or receptor site.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, phenyl, naphthyl, naphthalenyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof.

"Arylene" means a divalent aryl radical wherein aryl is as defined herein. "Arylene" includes, for example, ortho-, meta- and para-phenylene (1,2-phenylene, 1,3-phenylene and 1,4-phenylene respectively), which may be optionally substituted as defined herein.

"Arylalkyl" and "Aralkyl", which may be used interchangeably, mean a radical —R—R' where R is an alkylene group and R' is an aryl group as defined herein; e.g., benzyl, phenylethyl, 3-(3-chlorophenyl)-2-methylpentyl, and the like are examples of arylalkyl.

"Cycloalkyl" means a saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof such as cyclohexenyl, cyclopentenyl, and the like.

"Cycloalkylalkyl" means a moiety of the formula —R—R', where R is alkylene and R' is cycloalkyl as defined herein.

"Heteroalkyl" means an alkyl radical as defined herein wherein one, two or three hydrogen atoms have been replaced with a substituent independently selected from the group consisting of —$OR^a$, —$NR^bR^c$, and —$S(O)_nR^d$ (where n is an integer from 0 to 2), with the understanding that the point of attachment of the heteroalkyl radical is through a carbon atom, wherein $R^a$ is hydrogen, acyl, alkyl, cycloalkyl, or cycloalkylalkyl; $R^b$ and $R^c$ are independently of each other hydrogen, acyl, alkyl, cycloalkyl, or cycloalkylalkyl; and when n is 0, $R^d$ is hydrogen, alkyl, cycloalkyl, or cycloalkylalkyl, and when n is 1 or 2, $R^d$ is alkyl, cycloalkyl, cycloalkylalkyl, amino, acylamino, monoalkylamino, or dialkylamino. Representative examples include, but are not limited to, methoxy, ethoxy, 2-hydroxyethyl, 3-hydroxypropyl, 2-methoxyethyl, 3-methoxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroaryl" means a monocyclic or bicyclic monovalent radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyridinyl, pyridazyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof. The aforementioned heteroaryl moieties may be partially saturated. Thus, "heteroaryl" includes "imidazolinyl", tetrahydropyrimidinyl" and the like.

"Heteroarylene" means a divalent heteroaryl radical wherein heteroaryl is as defined herein. "Heteroarylene" may be optionally substituted as defined herein. "Heteroarylene" includes, for example, indolylene, pyrimidinylene, and the like.

The terms "halo" and "halogen", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —$CH_2Cl$, —$CH_2CF_3$, —$CH_2CCl_3$, perfluoroalkyl (e.g., —$CF_3$), and the like.

"Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, piperidinyl, piperazinyl, homopiperazinyl, azepinyl, pyrrolidinyl, pyrazolidinyl, imidazolinyl, imidazolidinyl, pyridinyl, pyridazinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like, including partially unsaturated derivatives thereof.

"Optionally substituted", when used in association with "aryl", phenyl", "heteroaryl", or "heterocyclyl", means an aryl, phenyl, heteroaryl, or heterocyclyl which is optionally substituted independently with one to four substituents, preferably one or two substituents selected from alkyl, cycloalkyl, cycloalkylalkyl, heteroalkyl, hydroxyalkyl, halo, nitro, cyano, hydroxy, alkoxy, amino, acylamino, mono-alkylamino, di-alkylamino, haloalkyl, haloalkoxy, heteroalkyl, —COR (where R is hydrogen, alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl), or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl.

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease state" means any disease, condition, symptom, or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

The terms "pro-drug" and "prodrug", which may be used interchangeably herein, refer to any compound which releases an active parent drug according to formula I in vivo when such prodrug is administered to a mammalian subject. Prodrugs of a compound of formula I are prepared by modifying one or more functional group(s) present in the compound of formula I in such a way that the modification(s) may be cleaved in vivo to release the parent compound. Prodrugs include compounds of formula I wherein a hydroxy, amino, or sulfhydryl group in a compound of Formula I is bonded to any group that may be cleaved in vivo to regenerate the free hydroxyl, amino, or sulfhydryl group, respectively. Examples of prodrugs include, but are not limited to, esters (e.g., acetate, formate, and benzoate derivatives), carbamates (e.g., N,N-dimethylaminocarbonyl) of hydroxy functional groups in compounds of formula I, N-acyl derivatives (e.g. N-acetyl) N-Mannich bases, Schiff bases and enaminones of amino functional groups, oximes, acetals, ketals and enol esters of ketone and aldehyde functional groups in compounds of Formula I, and the like, see Bundegaard, H. "Design of Prodrugs" p 1-92, Elsevier, New York-Oxford (1985), and the like.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. Those skilled in the art know how to choose a group for the ease of removal and for the ability to withstand the following reactions.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgement of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes:
(i) preventing the disease state, i.e. causing the clinical symptoms of the disease state not to develop in a subject that may be exposed to or predisposed to the disease state, but does not yet experience or display symptoms of the disease state.
(ii) inhibiting the disease state, i.e., arresting the development of the disease state or its clinical symptoms, or
(iii) relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature

In general, the nomenclature used in this Application is based on AUTONOM™ v. 4.0, a Beilstein Institute computerized system for the generation of IUPAC systematic nomenclature. Chemical structures shown herein were prepared using ISIS® version 2.2. Any open valency appearing on a carbon, oxygen or nitrogen atom in the structures herein indicates the presence of a hydrogen.

Compounds of the Invention

The invention provides compounds of the formula I: It should be understood that the scope of this invention encompasses not only the various isomers which may exist but also the various mixture of isomers which may be formed. Furthermore, the scope of the present invention also encompasses solvates and salts of compounds of formula I:

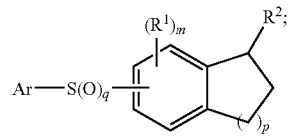

or a pharmaceutically acceptable salt thereof, wherein:
m is from 0 to 3;
p is from 1 to 3;
q is 0, 1, or 2;
Ar is optionally substituted aryl or optionally substituted heteroaryl;
each $R^1$ is independently halo, alkyl, haloalkyl, heteroalkyl, cyano, $-S(O)_q-R^a$, $-C(=O)-NR^bR^c$, $-SO_2-NR^bR^c$, $-N(R^d)C(=O)-R^e$, or $-C(=O)-R^e$, where q is from 0 to 2, $R^a$, $R^b$, $R^c$ and $R^d$ each independently is hydrogen or alkyl, and $R^e$ is hydrogen, alkyl, alkoxy or hydroxy;

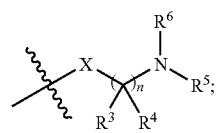

$R^2$ is
X is $-O-$ or $-NR^7-$;
n is 2 or 3;
$R^3$ and $R^4$ each independently is hydrogen or alkyl, or $R^3$ and $R^4$ together may form a $-C(O)-$;
$R^5$ and $R^6$ each independently is hydrogen or alkyl, or $R^5$ and $R^6$ together with the nitrogen to which they are attached may form a five- or six-membered ring that optionally includes an additional heteroatom selected from O, N and S, or one of $R^5$ and $R^6$ and one of $R^3$ and $R^4$ together with the atoms to which they are attached may form a five- or six-membered ring that optionally includes an additional heteroatom selected from O, N and S; and
$R^7$ is hydrogen or alkyl.

In certain embodiments of formula I, p is 1 or 2, and in specific embodiments p is 2. In many embodiments q is 2.

In certain embodiments, the compounds of the invention may be of formula II:

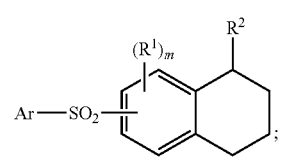

wherein m, Ar, $R^1$ and $R^2$ are as defined herein.

In some embodiments of formula I and formula II, p is 1 or 2, and in specific embodiments p is 1. In many embodiments m is 0 or 1, with $R^1$ preferably being halo. In certain embodiments Ar is optionally substituted aryl such as phenyl or naphthyl, each optionally substituted. In other embodiments Ar may be optionally substituted heteroaryl such as thienyl, pyridyl or pyrimidyl, each optionally substituted.

In certain embodiments of the invention, the compounds of formula I and formula II have n equal to 2 and X is —O—. In such embodiments $R^5$ and $R^6$ may both be hydrogen, or alternatively one of $R^5$ and $R^6$ may be hydrogen while the other is alkyl, preferably methyl. In other embodiments of formula I and formula II wherein n is 2 and X is —O—, $R^3$ and $R^4$ are hydrogen. In still other embodiments of formula I and formula II wherein n is 2 and X is —O—, $R^5$ and $R^6$ together with the nitrogen to which they are attached may form a ring of four to six members. In further embodiments of formula I and formula II wherein n is 2 and X is —O—, $R^3$ and $R^4$ together may form —C(O)—.

In certain embodiments of the invention, the compounds of formula I and formula II have n equal to 2 and X is —$NR^7$—. In such embodiments $R^5$ and $R^6$ may both be hydrogen, or alternatively one of $R^5$ and $R^6$ may be hydrogen while the other is alkyl, preferably methyl. In other embodiments of formula I and formula II wherein n is 2 and X is —$NR^7$—, $R^3$ and $R^4$ are hydrogen. In still other embodiments of formula I and formula II wherein n is 2 and X is —$NR^7$—, $R^5$ and $R^6$ together with the nitrogen to which they are attached may form a ring of four to six members. In further embodiments of formula I and formula II wherein n is 2 and X is —$NR^7$—, $R^3$ and $R^4$ together may form —C(O)—.

In certain embodiments of the invention, the compounds of formula I and formula II have n equal to 3 and X is —O—. In such embodiments $R^5$ and $R^6$ may both be hydrogen, or alternatively one of $R^5$ and $R^6$ may be hydrogen while the other is alkyl, preferably methyl. In other embodiments of formula I and formula II wherein n is 3 and X is —O—, $R^3$ and $R^4$ are hydrogen. In still other embodiments of formula I and formula II wherein n is 3 and X is —O—, $R^5$ and $R^6$ together with the nitrogen to which they are attached may form a ring of four to six members. In further embodiments of formula I and formula II wherein n is 3 and X is —O—, $R^3$ and $R^4$ together may form —C(O)—. In still further embodiments of formula I and formula II wherein n is 3 and X is —O—, one of $R^5$ and $R^6$ and one of $R^3$ and $R^4$ together with the atoms to which they are attached may form a ring of four to six members, preferably a six membered ring.

In certain embodiments of the invention, the compounds of formula I and formula II have n equal to 3 and X is —$NR^7$—. In such embodiments $R^5$ and $R^6$ may both be hydrogen, or alternatively one of $R^5$ and $R^6$ may be hydrogen while the other is alkyl, preferably methyl. In other embodiments of formula I and formula II wherein n is 3 and X is —$NR^7$—, $R^3$ and $R^4$ are hydrogen. In still other embodiments of formula I and formula II wherein n is 3 and X is —$NR^7$—, $R^5$ and $R^6$ together with the nitrogen to which they are attached may form a ring of four to six members. In further embodiments of formula I and formula II wherein n is 3 and X is —$NR^7$—, $R^3$ and $R^4$ together may form —C(O)—. In still further embodiments of formula I and formula II wherein n is 3 and X is —$NR^7$—, one of $R^5$ and $R^6$ and one of $R^3$ and $R^4$ together with the atoms to which they are attached may form a ring of four to six members, preferably a six membered ring.

In certain embodiments of formula I and formula II, $R^2$ may be aminoalkyl.

In certain embodiments of formula I and formula II, $R^2$ may be

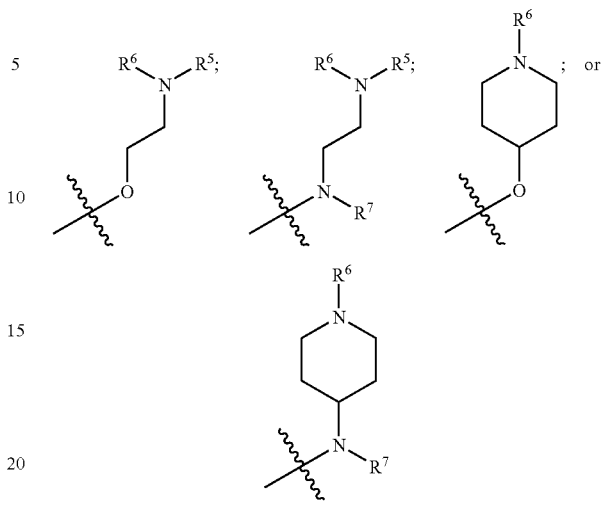

wherein $R^5$, $R^6$ and $R^7$ are as defined herein.

In certain embodiments, the compounds of the invention may be more specifically

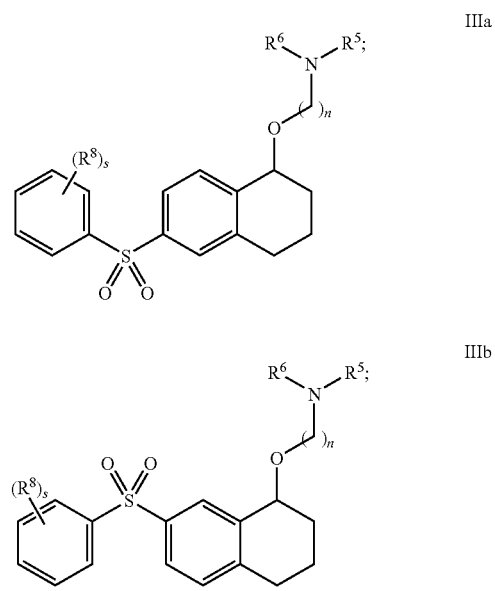

wherein:

s is from 0 to 4;

each $R^8$ is independently halo, alkyl, alkoxy, haloalkyl, heteroalkyl, cyano, —S(O)$_r$—$R^a$, —C(=O)—$NR^bR^c$, —SO$_2$—$NR^bR^c$, —N($R^d$)—C(=O)—$R^3$, or —C(=O)—$R^e$, where r is from 0 to 2, $R^a$, $R^b$, $R^c$, and $R^d$ each independently is hydrogen or alkyl, and $R^e$ is hydrogen, alkyl, alkoxy or hydroxy; and n, $R^5$ and $R^6$ are as defined herein.

In certain embodiments of formula IIIa or IIIb, s is from 0 to 2, and each $R^8$ is independently halo, alkyl, alkoxy, or haloalkyl. In many such embodiments, n is 2. Such compounds are more preferably of the formula IIIa. In such embodiments $R^5$ may be hydrogen and $R^6$ may be methyl.

Where any of $R^1$, $R^2$, $R^3$, $R^4$, $R^5$, $R^6$, $R^7$, $R^8$, $R^a$, $R^b$, $R^c$, $R^d$, and $R^e$ herein are alkyl or contain an alkyl moiety, such alkyl is preferably lower alkyl, i.e. $C_1$-$C_6$alkyl, and more preferably $C_1$-$C_4$alkyl.

Representative compounds in accordance with the invention are shown in Table 1 together with melting point or mass spectrum M+H, and the experimental examples (described below) associated with each compound. Melting points in many instances are shown for corresponding addition salts as indicated in Table 1.

TABLE 1

| # | Structure | Name | Mp or M + H |
|---|---|---|---|
| 1 | 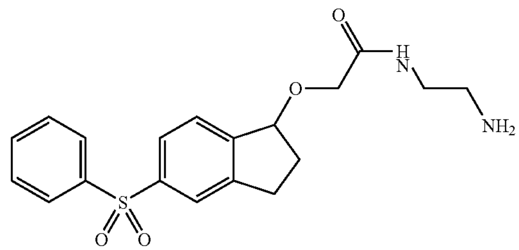 | N-(2-Amino-ethyl)-2-(5-benzenesulfonyl-indan-1-yloxy)-acetamide | 375 |
| 2 | 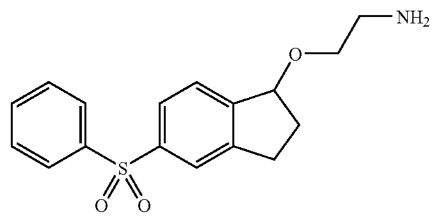 | 2-(5-Benzenesulfonyl-indan-1-yloxy)-ethylamine | 318 |
| 3 | 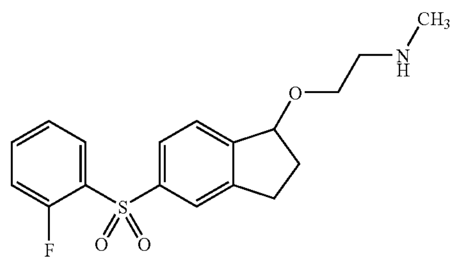 | {2-[5-(2-Fluoro-benzenesulfonyl)-indan-1-yloxy]-ethyl}-methyl-amine | 350 |
| 4 | 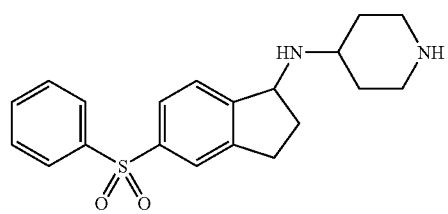 | (5-Benzenesulfonyl-indan-1-yl)-piperidin-4-yl-amine | 357 |
| 5 | 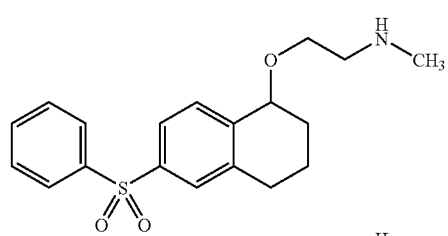 | [2-(6-Benzenesulfonyl-1,2,3,4-tetrahydro-naphthalen-1-yloxy)-ethyl]-methyl-amine | 346 |
| 6 | 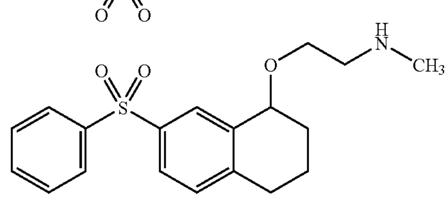 | [2-(7-Benzenesulfonyl-1,2,3,4-tetrahydro-naphthalen-1-yloxy)-ethyl]-methyl-amine | 346 |

TABLE 1-continued

| # | Structure | Name | Mp or M + H |
|---|---|---|---|
| 7 | 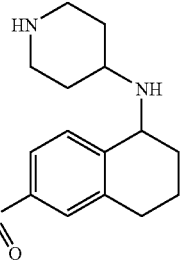 | (6-Benzenesulfonyl-1,2,3,4-tetrahydro-naphthalen-1-yl)-piperidin-4-yl-amine | 371 |
| 8 | 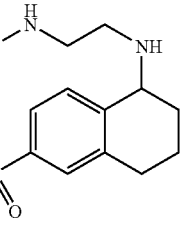 | N-(6-Benzenesulfonyl-1,2,3,4-tetrahydro-naphthalen-1-yl)-N'-methyl-ethane-1,2-diamine | 345 |
| 9 | 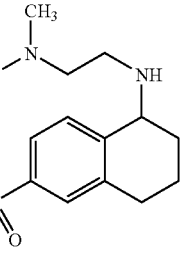 | N'-(6-Benzenesulfonyl-1,2,3,4-tetrahydro-naphthalen-1-yl)-N,N-dimethyl-ethane-1,2-diamine | 111.6–119.8° C. |
| 10 | 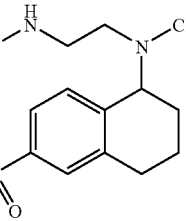 | N-(6-Benzenesulfonyl-1,2,3,4-tetrahydro-naphthalen-1-yl)-N,N'-dimethyl-ethane-1,2-diamine | 359 |

Another aspect of the invention provides a composition comprising a therapeutically effective amount of at least one compound of formula (I) and a pharmaceutically acceptable carrier.

Yet another aspect of the invention provides a method for treating a central em (CNS) disease state in a subject comprising administering to the subject a therapeutically effective amount of a compound of formula I. The disease state may comprise, psychoses, schizophrenia, manic depressions, neurological disorders, memory disorders, attention deficit disorder, Parkinson's disease, amyotrophic lateral sclerosis, Alzheimer's disease or Huntington's disease.

Still another aspect of the present invention provides a method for treating a disorder of the gastrointestinal tract in a subject comprising administering to the subject a therapeutically effective amount of a compound of formula (I).

Another aspect of the present invention provides a method for producing a compound of formula (I).

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as Fieser and Fieser's Reagents for Organic Synthesis; Wiley & Sons: New York, 1991, Volumes 1-15; Rodd's Chemistry of Carbon Compounds, Elsevier Science Publishers, 1989, Volumes 1-5 and Supplementals; and Organic Reactions, Wiley & Sons: New York, 2004, Volumes 1-56. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Scheme A below illustrates one synthetic procedure usable to prepare compounds of the invention, wherein X, Ar, m, p, q, $R^1$, $R^3$, $R^4$, $R^5$ and $R^6$ are as defined herein. Numerous synthetic routes to indanes and tetralins are known and may be used in preparation of the subject compounds, and the procedure of Scheme A is only exemplary. Specific examples of the procedure of Scheme A are provided in the following Experimental section.

SCHEME A

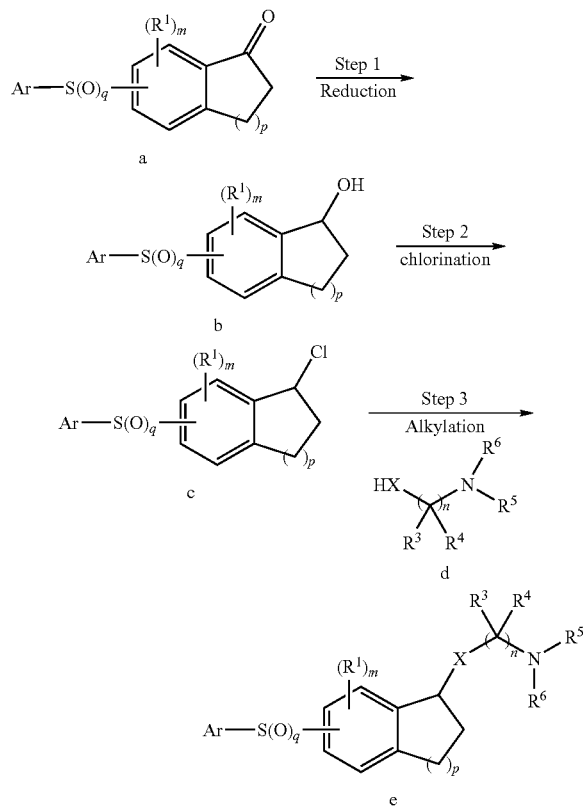

In step 1 of Scheme A, ketone compound a is reduced to give a corresponding alcohol compound b. Ketone compound may comprise, for example, an arylsulfonyl indanone where q is 2 and p 1, an arylsulfonyl tetralinone where q is 2 and p is 2, an arylsulfonyl benzoazepinone where q is 2 and p is 3, or like ketone in accordance with the invention. Corresponding, arylsulfanyl (q=0) and arylsulfinyl (q=1) ketone compounds may be used in this step. Ketone compounds a may be prepared by a variety of techniques known in the art, and specific examples of preparing such compounds are provided below in the Experimental section of this disclosure. The reduction reaction of step 1 may be achieved by treatment of ketone compound a with sodium borohydride under mild protic solvent conditions.

In step 2, alcohol compound b is subject to chlorination to provide nitrile chloro compound c. This reaction may be achieved using thionyl chloride under non-polar solvent conditions.

An alkylation reaction is carried out in step 3 by reaction of compound d with chlorine compound c to yield compound e, which is a compound of formula I in accordance with the invention. In compound d X may be —O— or —$NR^7$— where $R^7$ is as defined above. Where one or both of $R^5$ and $R^6$ are hydrogen, suitable protection and deprotection strategies may be employed in this step.

Many variations on the procedure of Scheme A are possible and will be readily apparent to those skilled in the art. In certain embodiments where X is O, steps 2 and 3 may be replaced with an O-alkylation reaction by treatment of compound b with a suitable aminoalkyl halide or a heteroalkyl halide that may subsequently be modified to introduce an amine functionality.

Specific details for producing compounds of formula I are described in the Examples section below.

Utility

The compounds of the invention have selective affinity for 5-HT receptors, including the $5\text{-}HT_6$ the $5\text{-}HT_{2A}$ receptor, or both, and as such are expected to be useful in the treatment of certain CNS disorders such as Parkinson's disease, Huntington's disease, anxiety, depression, manic depression, psychosis, epilepsy, obsessive compulsive disorders, mood disorders, migraine, Alzheimer's disease (enhancement of cognitive memory), sleep disorders, feeding disorders such as anorexia, bulimia, and obesity, panic attacks, akathisia, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such compounds are also expected to be of use in the treatment of certain GI (gastrointestinal) disorders such functional bowel disorder and irritable bowel syndrome.

Testing

The pharmacology of the compounds of this invention was determined by art recognized procedures. The in vitro techniques for determining the affinities of test compounds at the 5-HT6 receptor and the 5-HT2A receptor are described below.

Administration and Pharmaceutical Composition

The present invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the present invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

In general, compounds of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in Remington: The Science and Practice of Pharmacy 1995, edited by E. W. Martin, Mack Publishing Company, 19th edition, Easton, Pa. Representative pharmaceutical formulations containing a compound of the present invention are described in the Examples below.

EXAMPLES

The following preparations and examples are given to enable those skilled in the art to more clearly understand and to practice the present invention. They should not be considered as limiting the scope of the invention, but merely as being illustrative and representative thereof.

Preparation 1

6-Benzenesulfonyl-3,4-dihydro-2H-naphthalen-1-one

The synthetic procedure described in this Preparation was carried out according to the process shown in Scheme B.

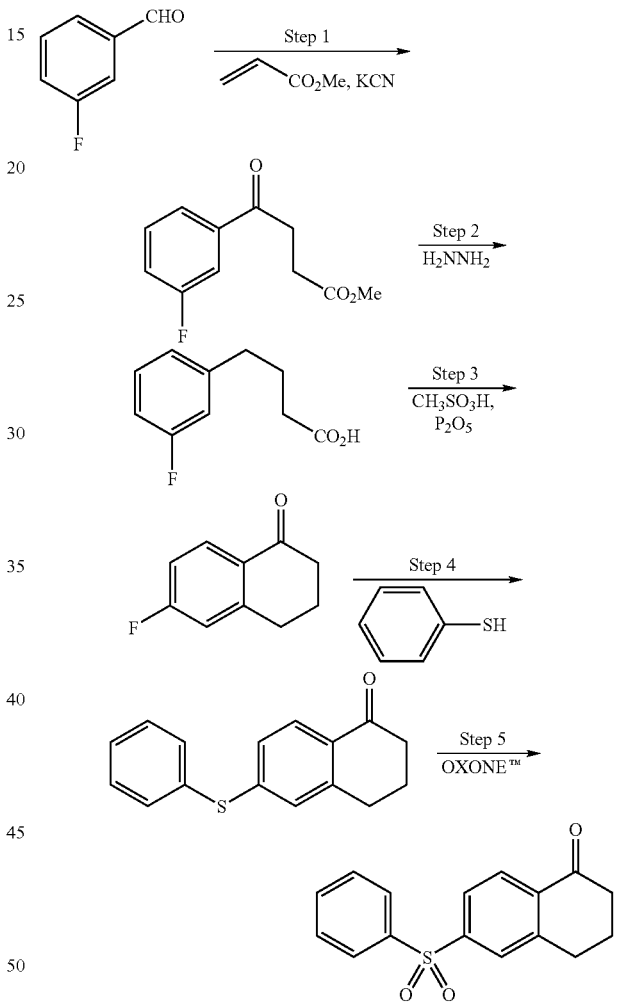

Step 1

4-(3-Fluoro-phenyl)-4-oxo-butyric Acid Methyl Ester

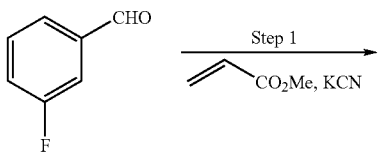

-continued

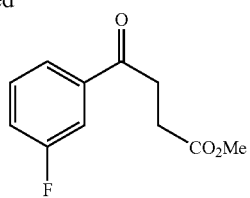

A solution of 3-fluorobenzaldehyde (35.38 g, 285.07 mml) in 35 mL dimethylformamide (DMF) was added to a heated (48° C.) solution of methyl acrylate (26.28 mL, 25.03 g, 290.7 mmol) and powdered KCN under Argon. The reaction mixture was stirred at 40° C. for 2 hours and then poured into 500 mL of water. This aqueous phase was extracted twice with 500 mL of $Et_2O$ and once with 250 mL of EtOAc. The combined organic layers were washed with water and saturated brine, and then dried over $MgSO_4$. The solvent was evaporated under reduced pressure to give 50.89 g (242.2 mmol, 84.93%) of 4-(3-fluoro-phenyl)-4-oxo-butyric acid methyl ester as an oil. MS: 211 $(M+H)^+$.

Step 2

4-(3-Fluoro-phenyl)-butyric Acid

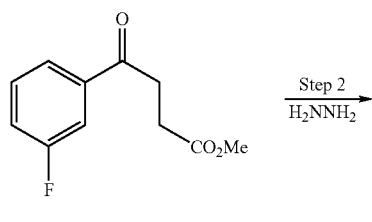

A solution of 4-(3-fluoro-phenyl)-4-oxo-butyric acid methyl ester (28.27 g, 134.49 mmol), hydrazine monohydrate (26.1 mL, 26.93 g, 537.96 mmol) and KOH (22.64 g, 403.47 mmol) in ethylene glycol (150 mL) was heated to reflux under argon and refluxed for 2 hours. The reaction mixture was cooled and diluted with 1.5 litres of water, 500 mL of $Et_2O$ was added, and the mixtures was acidified by addition of 6 M HCl with stirring, after which an additional 500 mL of $Et_2O$ was added. The organic layer was removed and the aqueous layer was extracted twice with 250 mL of 500 mL of $Et_2O$/EtOAc (3:1). The combined organic layers were washed with water, saturated brine, and then dried over $MgSO_4$. The solvent was evaporated under reduced pressure to yield a brownish oil, which was eluted through silica gel using hexanes/EtOAc (9:1). Removal of solvent under reduced pressure yielded 18.44 g (101.21 mmol, 75.26%) of 4-(3-fluoro-phenyl)-butyric acid as an oil. MS: 183 $(M+H)^+$.

Step 3

6-Fluoro-3,4-dihydro-2H-naphthalen-1-one

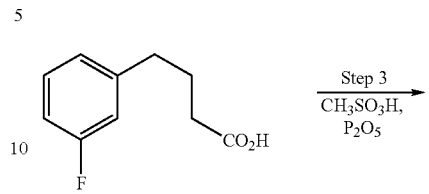

A solution of methanesulfonic acid (75 mL) and $P_2O_5$ was stirred at 85° C. for 15 minutes, at which point most of the $P_2O_5$ had dissolved. An additional 15 mL of methanesulfonic acid was added dropwise, and the mixture was stirred at 85° C. for 2 hours. The reaction mixture was poured into 500 mL of water and extracted twice with 400 mL of EtOAc. The combined organic layers were washed with saturated $NaHCO_3$, water, and saturated brine, and then dried over $MgSO_4$. The solvent was removed under reduced pressure to give an oil that was eluted through silica gel using hexanes/EtOAc (9:1). Removal of solvent under reduced pressure yielded 6.06 g, 36.91 mmol, 53.97%) of 6-fluoro-3,4-dihydro-2H-naphthalen-1-one as a yellow oil. MS: 165 $(M+H)^+$.

Step 4

6-Phenylsulfanyl-3,4-dihydro-2H-naphthalen-1-one

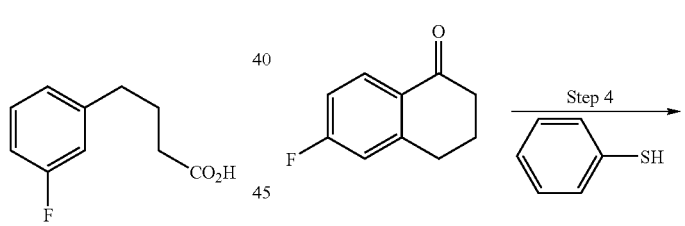

A solution of 6-fluoro-3,4-dihydro-2H-naphthalen-1-one (5.51 g, 33.56 mmol), benzenethiol (4.07 g, 3.79 mL, 36.92 mmol) and $K_2CO_3$ (9.28 g, 67.12 mmol) in 50 mL of N-methyl pyrrolidinone (NMP) was heated to 80° C. under argon and stirred at 80° C. for 2 hours. The reaction mixture was poured into 500 mL of water and diluted with 300 mL of EtOAc. The layers were separated and the aqueous layer was extracted twice with 250 mL of EtOAc. The combined organic layers were washed with water, saturated brine, and then dried over $MgSO_4$. The solvent was removed under reduced pressure to yield an oil which was eluted through silica gel using hexanes/EtOAc (9:1). Removal of solvent under reduced pressure provided 8.05 g (31.65 mmol, 94.31%) of 6-phenylsulfanyl-3,4-dihydro-2H-naphthalen-1-one as a pale yellow oil. MS: 255 $(M+H)^+$.

Step 5

6-Benzenesulfonyl-3,4-dihydro-2H-naphthalen-1-one

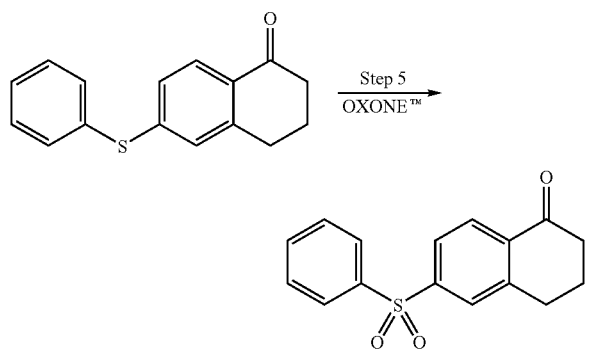

A solution of 6-phenylsulfanyl-3,4-dihydro-2H-naphthalen-1-one (8.05 g, 31.65 mmol) in MeOH/MeCN (50 mL of each) was stirred at room temperature. OXONE™ (potassium peroxymonosulfate, 77.83 g, 126.60 mmol) was dissolved in 50 mL of water and was added to the stirring reaction. The reaction mixture was stirred for 15 hours, and then evaporated under reduced pressure. The resulting aqueous residue was diluted with 500 mL of water and extracted three times with 300 mL of EtOAc. The combined extracts were washed with water, saturated brine, and dried over $MgSO_4$. The solvent was removed under reduced pressure to yield an oil which was eluted through silica gel with hexane followed by chloroform. Removal of solvent under reduced pressure afforded 6.55 g (22.87 mmol, 72.27%) of 6-benzenesulfonyl-3,4-dihydro-2H-naphthalen-1-one as a white solid, which was recrystallized from $EtO_2$/hexanes. MS: 287 $(M+H)^+$.

Similarly prepared using the above procedure with 3-chlorobenzenethiol in step 4, was 6-(3-chloro-benzenesulfonyl)-3,4-dihydro-2H-naphthalen-1-one. MS: 287 $(M+H)^+$.

Preparation 2

7-Benzenesulfonyl-3,4-dihydro-2H-naphthalen-1-one

The synthetic procedure described in this Preparation was carried out according to the process shown in Scheme C.

SCHEME C

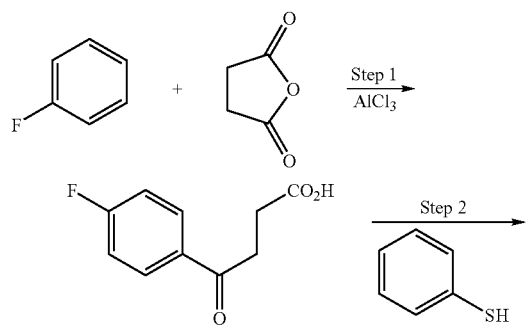

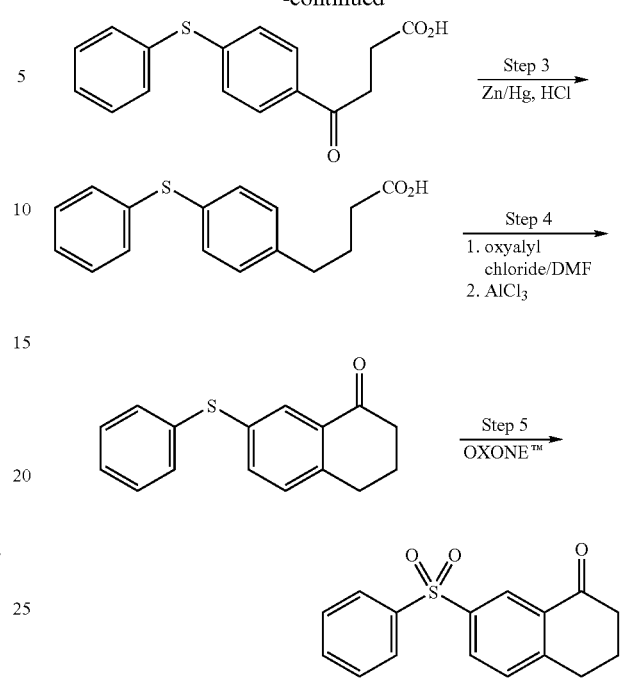

Step 1:

4-(4-Fluoro-phenyl)-4-oxo-butyric Acid

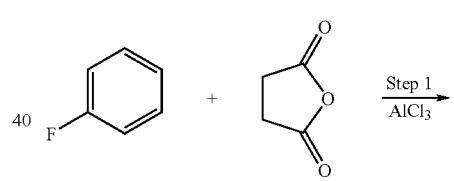

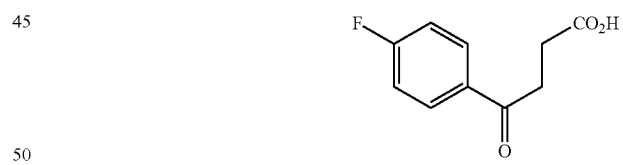

Fluorobenzene (50 mL, 530 mmol) and aluminum trichloride (156 g, 1.17 mol) were added to 500 mL of methylene chloride, and the reaction mixture was stirred. Succinic anhydride (50 g, 500 mmol) was added to the stirring reaction mixture all at once, and the reaction mixture was stirred at room temperature for 2 hours. The reaction was quenched by cautious addition of 10% HCl, and the reaction mixture was added to 500 mL of water. The aqueous mixture was extracted twice with 250 mL of methylene chloride, and the combined organic layers were dried ($MgSO_4$), and evaporated under reduced pressure to give 62 g (316 mmol, 59.6%) of 4-(4-fluoro-phenyl)-4-oxo-butyric acid as a crude solid. MS: 197 $(M+H)^+$.

Step 2:

4-Oxo-4-(4-phenylsulfanyl-phenyl)-butyric Acid

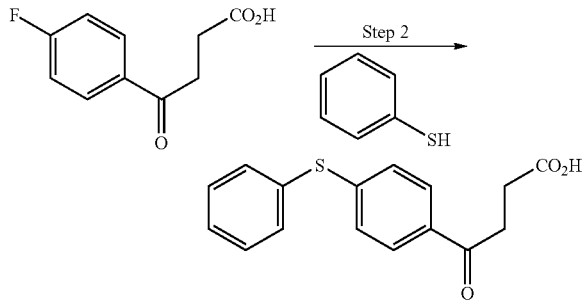

4-(4-Fluoro-phenyl)-4-oxo-butyric acid (10.0 g, 51 mmol), thiophenol (5.2 g, 51 mmol) and powdered potassium carbonate (13.8 g, 100 mmol) were added to 25 mL of dimethyl sulfoxide (DMSO). The reaction mixture was heated to 110° C. for 2 hours, then cooled and diluted by addition of 250 mL water. The aqueous mixture was extracted three times with 100 mL of EtOAc, and the combined organic layers were dried (MgSO$_4$), and evaporated under reduced pressure to yield 11 g (38.5 mmol, 75.5%) of 4-oxo-4-(4-phenylsulfanyl-phenyl)-butyric acid as a crude solid. MS: 287 (M+H)$^+$.

Step 3:

4-(4-Phenylsulfanyl-phenyl)-butyric Acid

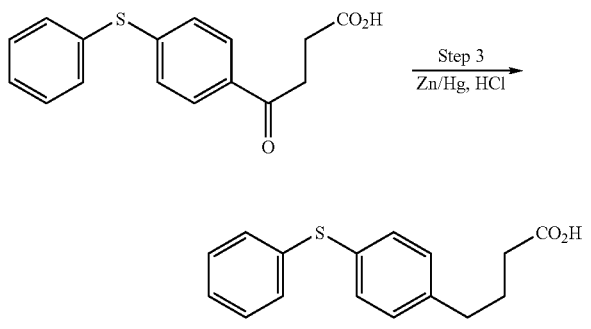

Powdered Zinc (66 g) was washed with 2% HCl, added to a solution of HgCl$_2$ (6 g) in 50 mL of 6M HCl. This mixture was shaken vigorously for 5 minutes, and excess liquid was decanted. The mixture was then added to a mechanically stirred suspension of 4-oxo-4-(4-phenylsulfanyl-phenyl)-butyric acid (6.5 g, 22.7 mmol) in 450 mL of 6M HCl, and the reaction mixture was stirred at room temperature for 5 days. The mixture was then decanted to remove excess HCl, and quenched by addition of 250 mL water. The aqueous mixture was extracted three times with 100 mL of EtOAc, and the combined organic layers were dried under reduced pressure to yield 5.0 g (18.4 mmol, 81%) of 4-(4-phenylsulfanyl-phenyl)-butyric acid as a crude solid. MS: 273 (M+H)$^+$.

Step 4:

7-Phenylsulfanyl-3,4-dihydro-2H-naphthalen-1-one

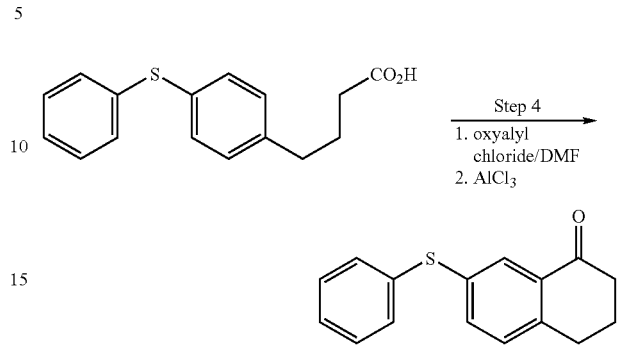

4-(4-Phenylsulfanyl-phenyl)-butyric acid (5.0 g, 18.4 mmol) was dissolved in 50 mL tetrahydrofuran (THF). Oxalyl chloride (1.8 mL, 20 mmol) and one drop of DMF were added, and the reaction mixture was stirred for 1 hour, and then evaporated to dryness under reduced pressure. The resulting residue was dissolved in 40 mL of 1,2-dichloroethane, and aluminum trichloride (0.85 g, 25 mmol) was added all at once. The reaction mixture was stirred for 1 hour, and quenched by addition of 2% HCl. This aqueous mixture was extracted twice with 100 mL of EtOAc, and the combined organic layers were dried (MgSO$_4$) and evaporated to yield 2.54 g (10 mmol, 55.5%) of 7-phenylsulfanyl-3,4-dihydro-2H-naphthalen-1-one as a gummy residue. MS: 255 (M+H)$^+$.

Step 5:

7-Benzenesulfonyl-3,4-dihydro-2H-naphthalen-1-one

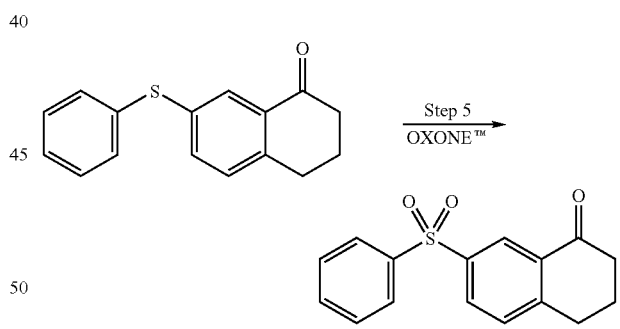

7-Phenylsulfanyl-3,4-dihydro-2H-naphthalen-1-one ( ) was dissolved in 50 mL of MeOH and stirred at room temperature. OXONE™ (13.5 g, 22 mmol) was dissolved in 10 mL of water and added to the stirring reaction. The reaction mixture was stirred for 8 hours, and then evaporated under reduced pressure. The resulting aqueous residue was diluted with 200 mL of water and extracted three times with 100 mL of EtOAc. The combined extracts were dried over MgSO$_4$, and the solvent was removed under reduced pressure to yield an oil which was eluted through silica gel with 1:1 EtOAc/hexanes. Removal of solvent under reduced pressure afforded 1.7 g (5.9 mmol, 59%) of 7-benzenesulfonyl-3,4-dihydro-2H-naphthalen-1-one as an oil. MS: 287 (M+H)$^+$.

Similarly prepared using the above procedure with 4-fluorobenzenethiol in step 2, was 7-(4-fluoro-benzenesulfonyl)-3,4-dihydro-2H-naphthalen-1-one. MS: 287 (M+H)+.

Preparation 3

5-Phenylsulfonyl-indan-1-one

The synthetic procedure described in this Preparation was carried out according to the process shown in Scheme D.

SCHEME D

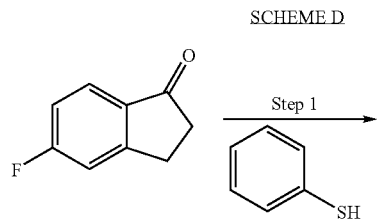

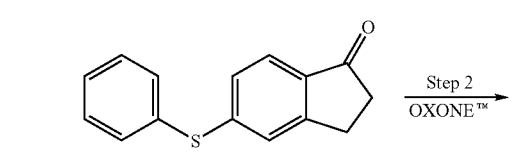

Step 1:

5-Phenylsulfanyl-indan-1-one

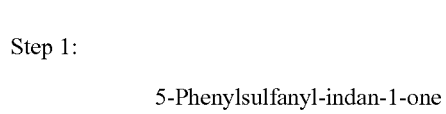

5-Fluoro-1-indanone from Aldrich Sigma Chemical Co. (Cat No. 18,566-3) was treated with benzenethiol in the presence of potassium carbonate using the procedure of step 4 of Example 1 to afford 5-phenylsulfanyl-indan-1-one. MS: 241 (M+H)+.

Step 2:

5-Phenylsulfonyl-indan-1-one

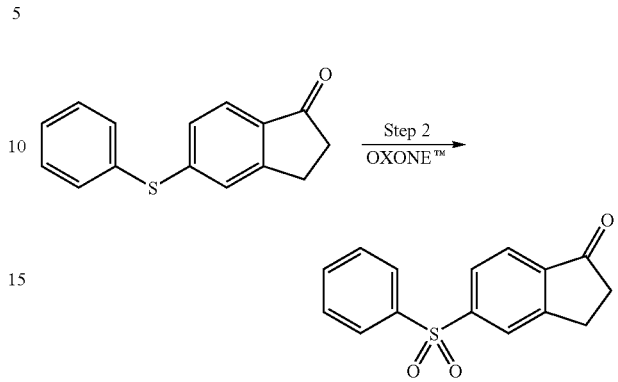

5-Phenylsulfanyl-indan-1-one was treated with OXONE™ using the procedure of step 5 of Example 1 to afford 5-phenylsulfonyl-indan-1-one. MS: 273 (M+H)+.

Example 1

[2-(6-Benzenesulfonyl-1,2,3,4-tetrahydro-naphthalen-1-yloxy)-ethyl]-methyl-amine The synthetic procedure described in this Example was carried out according to the process shown in Scheme E.

SCHEME E

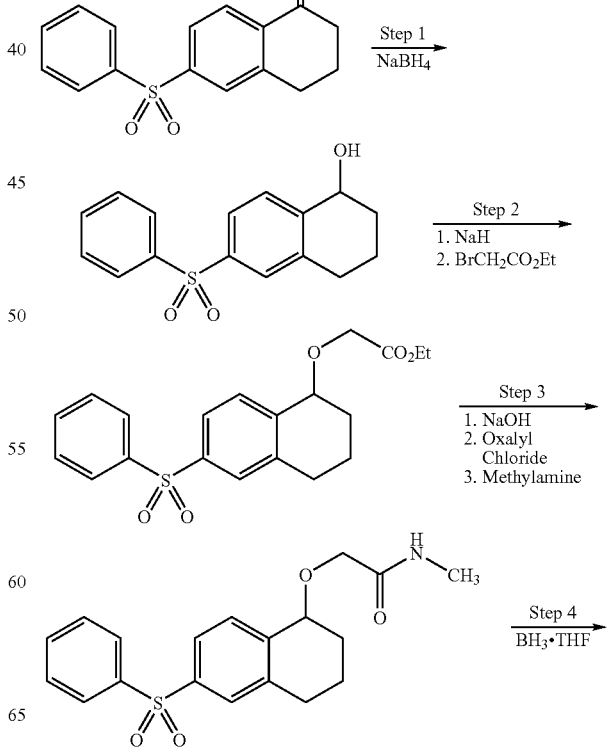

-continued

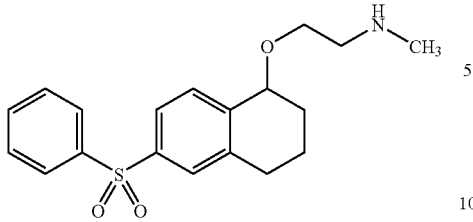

Step 1

6-Benzenesulfonyl-1,2,3,4-tetrahydro-naphthalen-1-ol

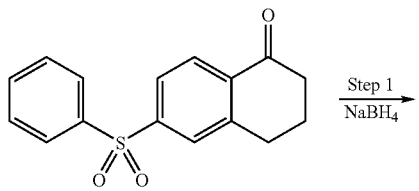

-continued

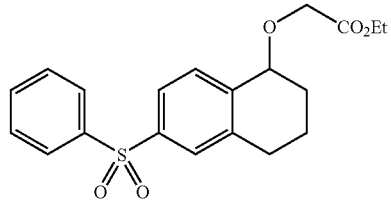

6-Benzenesulfonyl-1,2,3,4-tetrahydro-naphthalen-1-ol (1.2 g, 4.16 mmol) was dissolved in 60 mL of dry DMF, and the reaction mixture was cooled in an ice bath. Sodium hydride (0.2 g of 60% solid in oil, washed with hexanes) was added, and the reaction mixture was stirred under nitrogen for 20 minutes. Ethyl bromoacetate (0.55 mL) was added dropwise, and stirring was continued for three hours, during which time the reaction mixture was allowed to warm to room temperature. Water (250 mL) was added to the reaction mixture, and the aqueous mixture was extracted twice with 150 mL of EtOAc. The combined organic layers were washed with water, brine, dried over $MgSO_4$, and the solvent was removed under reduced pressure to yield an oil which was eluted through silica gel under medium pressure with 4:1 EtOAc/hexanes. Removal of solvent under reduced pressure afforded 0.75 g (2.0 mmol, 48%) of (6-benzenesulfonyl-1,2,3,4-tetrahydro-naphthalen-1-yloxy)-acetic acid ethyl ester as an oil. MS: 375 $(M+H)^+$.

Step 3

2-(6-Benzenesulfonyl-1,2,3,4-tetrahydro-naphthalen-1-yloxy)-N-methyl-acetamide

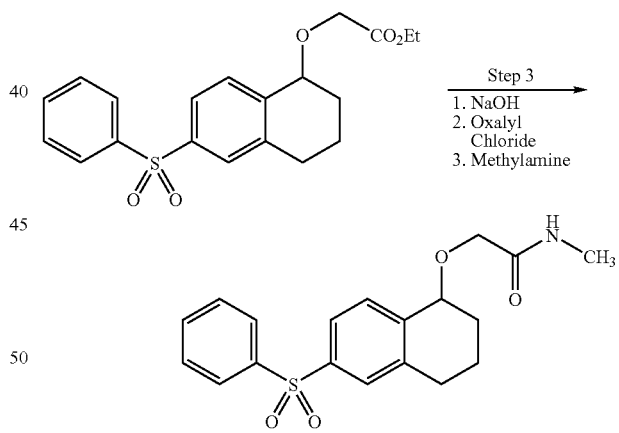

6-Benzenesulfonyl-3,4-dihydro-2H-naphthalen-1-one (1.31 g, 4.6 mmol) and sodium borohidride (0.35 g, 9.3 mmol) were added to 50 mL methanol, and the reaction mixture was stirred at room temperature for one hour. Water (200 mL was then added to the reaction mixture, resulting in precipitation of white crystals, which were collected by filtration and dried under $N_2$ to give 1.2 g (4.16 mmol, 90%) of 6-benzenesulfonyl-1,2,3,4-tetrahydro-naphthalen-1ol, MS: 289 $(M+H)^+$.

Step 2

(6-Benzenesulfonyl-1,2,3,4-tetrahydro-naphthalen-1-yloxy)-acetic Acid Ethyl Ester

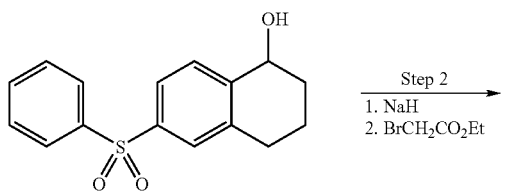

(6-Benzenesulfonyl-1,2,3,4-tetrahydro-naphthalen-1-yloxy)-acetic acid ethyl ester (0.75 g, 2.0 mmol) was dissolved in 25 mL of methanol, and aqueous NaOH (15 mL of 25% solution) was added. The reaction mixture was heated to 50° C. for ten minutes, then cooled, diluted with 20 mL water, and acidified by addition of 1N HCl. The resulting aqueous mixture was extracted three times with 100 mL of EtOAc. The combined organic layers were washed with water, brine, dried over $MgSO_4$, and the solvent was removed under reduced pressure. To the resulting residue was dissolved in 30 mL dry tetrahydrofuran (THF), and oxalyl chloride (0.8 mL) and dimethylformamide (one drop) were added. The reaction mixture was stirred for four hours under nitrogen at room temperature, after which solvent was removed under reduced pressure. The residue was dissolved in 25 mL of dioxane, and the resulting solution was added dropwise to a solution of 2.0 g methylamine hydrochloride in 25 mL 1N NaOH at 0° C. The resulting precipitate was collected and air dried, and eluted through silica gel under medium pressure with 4:1 EtOAc/hexanes. Removal of solvent under reduced pressure afforded 0.6 g (1.67 mmol, 83.5%) of (2-(6-benzenesulfonyl-1,2,3,4-tetrahydro-naphthalen-1-yloxy)-N-methyl-acetamide as an oil. MS: 360 (M+H)+.

Step 4

[2-(6-Benzenesulfonyl-1,2,3,4-tetrahydro-naphthalen-1-yloxy)-ethyl]-methyl-amine

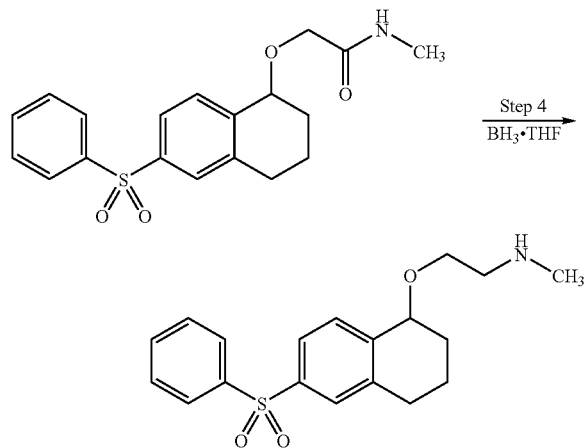

(2-(6-Benzenesulfonyl-1,2,3,4-tetrahydro-naphthalen-1-yloxy)-N-methyl-acetamide (0.7 g, 1.9 mmol) was dissolved in 25 mL of dry THF. Borane (10 mL of 1N THF solution) was added, and the reaction mixture was refluxed for three hours under nitrogen. The reaction mixture was cooled and 25 mL of 25% aqueous HCl was added. The reaction mixture was refluxed for 10 minutes, cooled, and solvent was removed under reduced pressure. The aqueous residue was basified by dropwise addition of 1N aqueous NaOH, and the aqueous mix was extracted three times with 50 mL of EtOAc. The combined organic layers were washed with water, brine, and dried over MgSO4. The residue was recrystallized from Et2O/MeOH/HCl to give 380 mg (1.1 mmol, 58%) of [2-(6-benzenesulfonyl-1,2,3,4-tetrahydro-naphthalen-1-yloxy)-ethyl]-methyl-amine hydrochloride. MS: 346 (M+H)+.

Similarly prepared, starting with 5-(2-fluorophenylsulfonyl)-indan-1-one and 7-benzenesulfonyl-3,4-dihydro-2H-naphthalen-1-one respectively in step 1, were:

{2-[5-(2-Fluoro-benzenesulfonyl)-indan-1-yloxy]-ethyl}-methyl-amine, MS: 350 (M+H)+; and

[2-(7-Benzenesulfonyl-1,2,3,4-tetrahydro-naphthalen-1-yloxy)-ethyl]-methyl amine, MS: 346 (M+H)+.

Example 2

N-(6-Benzenesulfonyl-1,2,3,4-tetrahydro-naphthalen-1-yl)-N'-methyl-ethane-1,2-diamine The synthetic procedure described in this Example was carried out according to the process shown in Scheme F.

Scheme F

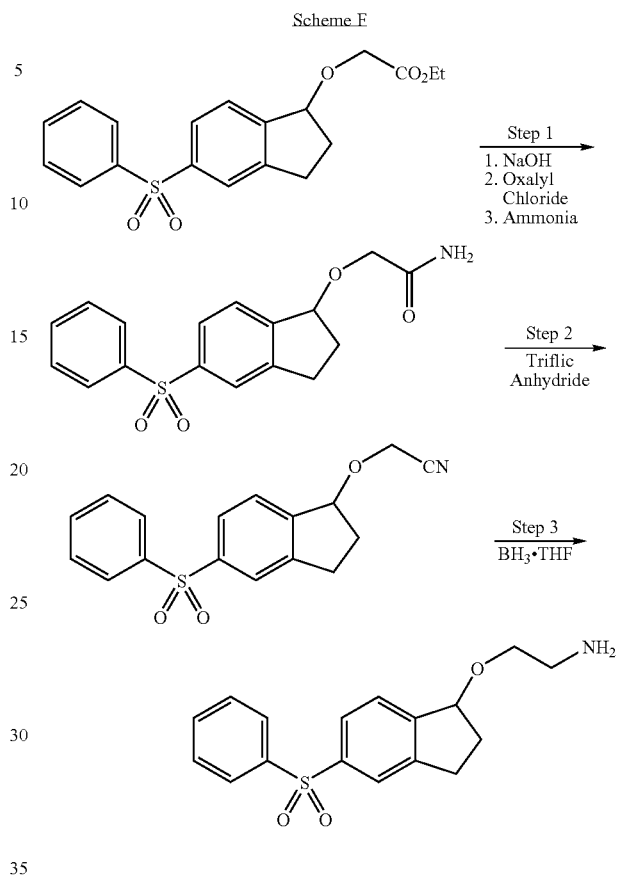

Step 1

2-(5-Benzenesulfonyl-indan-1-yloxy)-acetamide

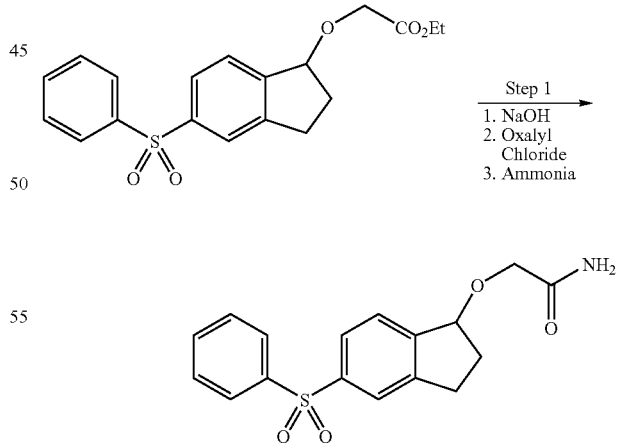

2-(5-Benzenesulfonyl-indan-1-yloxy)-acetamide was prepared from (6-benzenesulfonyl-1,2,3,4-tetrahydro-naphthalen-1-yloxy)-acetic acid ethyl ester using the procedure of step 3 of Example 1, but replacing the methylamine hydrochloride with ammonia. MS: 332 (M+H)+.

Step 2

(5-Benzenesulfonyl-indan-1-yloxy)-acetonitrile

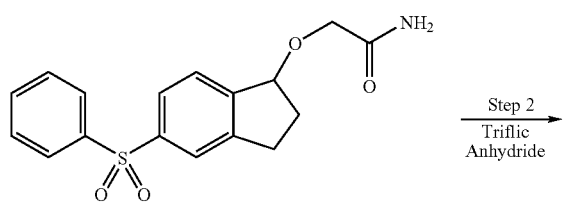

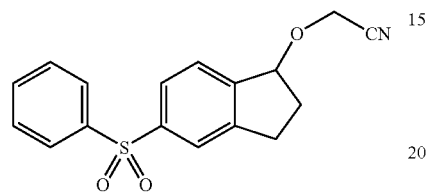

2-(5-Benzenesulfonyl-indan-1-yloxy)-acetamide (1.1 g, 3.3 mmol) was dissolved in 10 mL pyridine, and the reaction mixture was stirred and cooled in an ice bath. Trifluoromethanesulfonyl anhydride (2 mL) was added dropwise, and the reaction mixture was allowed to warm to room temperature. The reaction was quenched by additions of 100 mL of 10% aqueous HCl, and the aqueous phase was extracted twice with 150 mL of EtOAc. The combined organic layers were washed with water, brine, and dried over MgSO$_4$, and the residue was purified by medium pressure chromatography eluting through silica gel using EtOAc/Hexanes (1:5) to give 0.5 g (1.6 mmol, 48.5%) of (5-benzenesulfonyl-indan-1-yloxy) acetonitrile. MS: 314 (M+H)$^+$.

Step 3

N-(6-Benzenesulfonyl-1,2,3,4-tetrahydro-naphthalen-1-yl)-N'-methyl-ethane-1,2-diamine

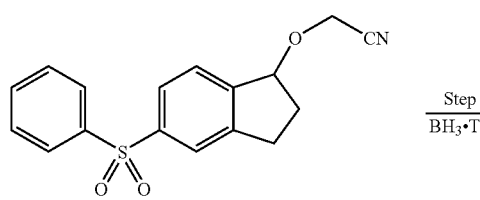

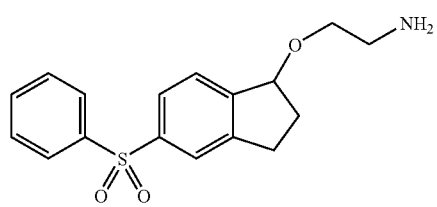

(5-Benzenesulfonyl-indan-1-yloxy)-acetonitrile was reduced to N-(6-benzenesulfonyl-1,2,3,4-tetrahydro-naphthalen-1-yl)-N'-methyl-ethane-1,2-diamine using borane in THF following the procedure of step 4 of Example 1. MS: 318 (M+H)$^+$.

Example 3

N-(6-Benzenesulfonyl-1,2,3,4-tetrahydro-naphthalen-1-yl)-N'-methyl-ethane-1,2-diamine The synthetic procedure described in this Example was carried out according to the process shown in Scheme G.

Scheme G

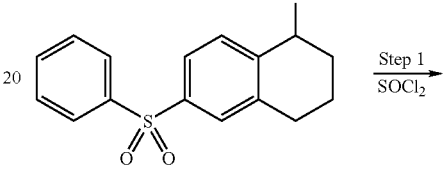

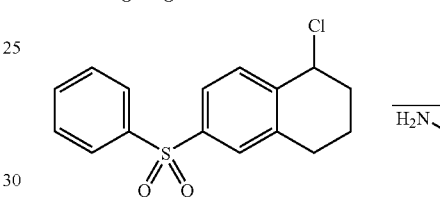

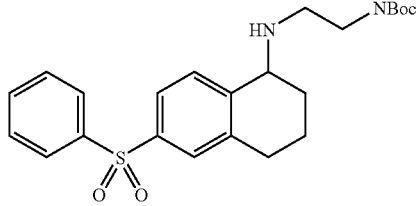

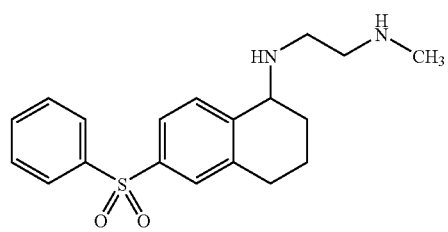

Step 1

6-Benzenesulfonyl-1-chloro-1,2,3,4-tetrahydro-naphthalene

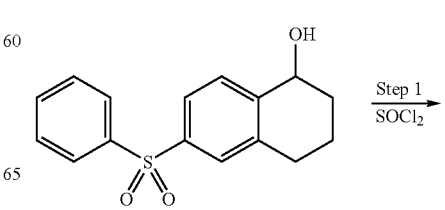

-continued

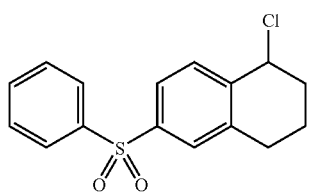

6-Benzenesulfonyl-1,2,3,4-tetrahydro-naphthalen-1-ol (0.65 g, 2.26 mmol) was dissolved in 50 mL toluene, and 1 mL of thionyl chloride was added. The reaction was refluxed for one hour, and then cooled. Solvent was removed under reduced pressure to yield 6-benzenesulfonyl-1-chloro-1,2,3,4-tetrahydro-naphthalene (0.6 g, 86.3%) as a crude oil. MS: 308 (M+H)+.

Step 2

[2-(6-Benzenesulfonyl-1,2,3,4-tetrahydro-naphthalen-1-ylamino)-ethyl]-methyl-carbamic Acid tert-butyl Ester

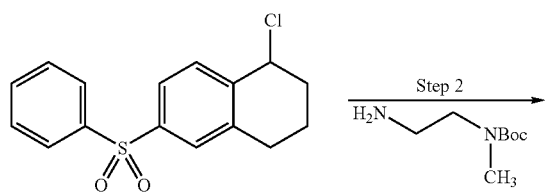

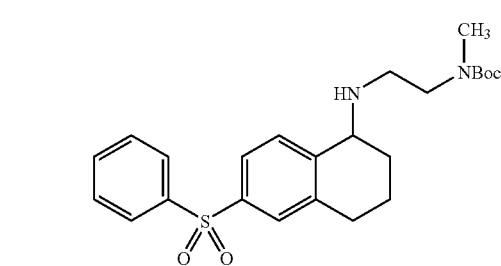

6-Benzenesulfonyl-1-chloro-1,2,3,4-tetrahydro-naphthalene (0.6 g, 1.95 mmol), (2-Amino-ethyl)-methyl-carbamic acid tert-butyl ester (0.512 g, 2.925 mmol), sodium iodide (0.1 g) and potassium carbonate (0.5 g) were added to 50 mL of acetonitrile, and the reaction mixture was refluxed for 120 hours. The reaction mixture was cooled and diluted with 200 mL of water. The aqueous mix was extracted twice with 200 mL of EtOAc, and the combined organic layers were washed with water, brine, and dried over MgSO4. Solvent was removed under reduced pressure, and the resulting oil was eluted through silica gel (medium pressure chromatography) eluting with EtOAc/Hexanes 20%/80%. Removal of solvent under reduced pressure afforded 0.4 g (0.9 mmol, 46%) of [2-(6-benzenesulfonyl-1,2,3,4-tetrahydro-naphthalen-1-ylamino)-ethyl]-methyl-carbamic acid tert-butyl ester as an oil. MS: 446 (M+H)+.

Step 3

N-(6-Benzenesulfonyl-1,2,3,4-tetrahydro-naphthalen-1-yl)-N'-methyl-ethane-1,2-diamine

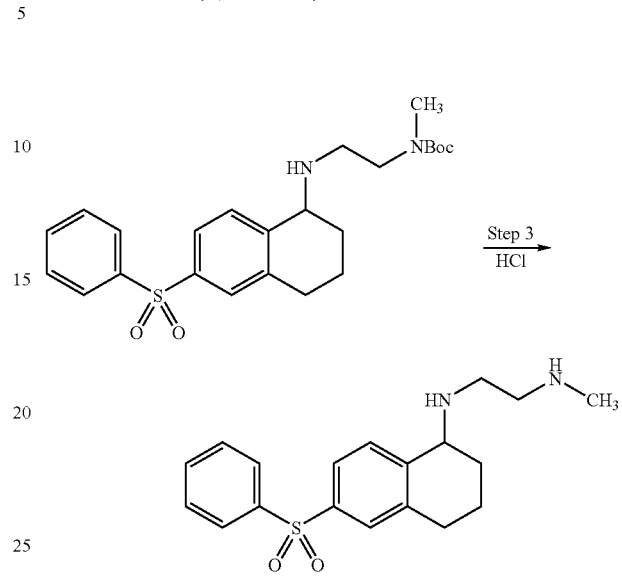

[2-(6-Benzenesulfonyl-1,2,3,4-tetrahydro-naphthalen-1-ylamino)-ethyl]-methyl-carbamic acid tert-butyl ester (0.4 g, 0.9 mmol) was dissolved in 20 mL of tetrahydrofuran, and 20 mL of 10% HCl in Et2O was added. The reaction mixture was refluxed for one hour and then cooled. The solvent was evaporated under reduced pressure, and the resulting solid was recrystallized from EtOH-Et2O to yield 0.3 g (0.87 mmol, 97%) of N-(6-benzenesulfonyl-1,2,3,4-tetrahydro-naphthalen-1-yl)-N'-methyl-ethane-1,2-diamine as a hydrochloride salt. MS: 345 (M+H)+.

Additional compounds prepared by the procedure of Example 3 are shown in Table 1.

Example 4

Formulations

Pharmaceutical preparations for delivery by various routes are formulated as shown in the following Tables. "Active ingredient" or "Active compound" as used in the Tables means one or more of the Compounds of Formula I.

| Composition for Oral Administration | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration | |
|---|---|
| Ingredient | Amount |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation | |
|---|---|
| Ingredient | % wt./wt. |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation | |
|---|---|
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

| Topical Formulation | |
|---|---|
| Ingredients | grams |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

Example 5

Radioligand Binding Studies

This example illustrates in vitro radioligand binding studies of compound of formula I.

The binding activity of compounds of this invention in vitro was determined as follows. Duplicate determinations of 5-$HT_6$ ligand affinity were made by competing for binding of [$^3$H]LSD in cell membranes derived from HEK293 cells stably expressing recombinant human 5-$HT_6$ receptor. Duplicate determinations of 5-HT2A ligand affinity were made by competing for binding of [$^3$H]Ketanserin (3-(2-(4-(4-fluorobenzoyl)piperidinol)ethyl)-2,4(1H,3H)-quinazolinedione) in cell membranes derived from CHO-K1 cells stably expressing recombinant human 5-$HT_{2A}$ receptor. Membranes were prepared from HEK 293 cell lines by the method described by Monsma et al., Molecular Pharmacology, Vol. 43 pp. 320-327 (1993), and from CHO-K1 cell lines as described by Bonhaus et al., Br J Pharmacol. June 115(4): 622-8 (1995).

For estimation of affinity at the 5-$HT_6$ receptor, all determinations were made in assay buffer containing 50 mM Tris-HCl, 10 mM $MgSO_4$, 0.5 mM EDTA, 1 mM ascorbic acid, pH 7.4 at 37° C., in a 250 microliter reaction volume. For estimation of affinity at the 5-HT2A receptor all determinations were made in assay buffer containing 50 mM Tris-HCl, 5 mM ascorbic acid, 4 mM CaCl2, pH 7.4 at 32° C., in a 250 microliter reaction volume.

Assay tubes containing [³H] LSD or [³H]Ketanserin (5 nM), competing ligand, and membrane were incubated in a shaking water bath for 75 min. at 37° C. (for 5-HT$_6$) or 60 min. at 32° C. (for 5-HT2A), filtered onto Packard GF-B plates (pre-soaked with 0.3% PEI) using a Packard 96 well cell harvester and washed 3 times in ice cold 50 mM Tris-HCl. Bound [³H] LSD or [³H]Ketanserin were determined as radioactive counts per minute using Packard TopCount.

Displacement of [³H]LSD or [³H]Ketanserin from the binding sites was quantified by fitting concentration-binding data to a 4-parameter logistic equation:

$$\text{binding} = \text{basal} + \left(\frac{B\text{max} - \text{basal}}{1 + 10^{-Hill(\log[ligand] - \log IC_{50})}}\right)$$

where Hill is the Hill slope, [ligand] is the concentration of competing radioligand and IC$_{50}$ is the concentration of radioligand producing half-maximal specific binding of radioligand. The specific binding window is the difference between the Bmax and the basal parameters.

Using the procedures of this Example, compounds of Formula I were tested and found to be selective 5-HT$_6$ antagonists, selective 5-HT2A antagonists, or both. For example, the compound 2-(6-Benzenesulfonyl-1,2,3,4-tetrahydro-naphthalen-1-yloxy)-ethyl]-methyl-amine exhibited a pKi of 8.74 for the 5-HT$_6$ receptor, and a pKi of 7.21 for the 5-HT2A receptor.

Example 6

Cognition Enhancement

The cognition-enhancing properties of compounds of the invention may be in a model of animal cognition: the object recognition task model. 4-month-old male Wistar rats (Charles River, The Netherlands) were used. Compounds were prepared daily and dissolved in physiological saline and tested at three doses. Administration was always given i.p. (injection volume 1 ml/kg) 60 minutes before T1. Scopolamine hydrobromide was injected 30 minutes after compound injection. Two equal testing groups were made of 24 rats and were tested by two experimenters. The testing order of doses was determined randomly. The experiments were performed using a double blind protocol. All rats were treated once with each dose condition. The object recognition test was performed as described by Ennaceur, A., Delacour, J., 1988, A new one-trial test for neurobiological studies of memory in rats. 1: Behavioral data. *Behav. Brain Res.* 31, 47-59.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound of formula I:

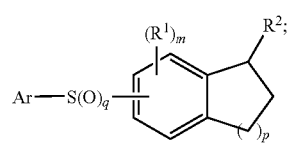

or a pharmaceutically acceptable salt thereof, wherein:
m is from 0 to 3;
p is from 1 to 3;
q is 0, 1 or 2;
Ar is optionally substituted aryl or optionally substituted heteroaryl;
each R$^1$ is independently halo, alkyl, haloalkyl, heteroalkyl, cyano, —S(O)$_q$R$^a$, —C(=O)—NR$^b$R$^c$, —SO$_2$—NR$^b$R$^c$, —N(R$^d$)—C(=O)—R$^e$, or —C(=O)—R$^e$, where q is from 0 to 2, R$^a$, R$^b$, R$^c$ and R$^d$ each independently is hydrogen or alkyl, and R$^e$ is hydrogen, alkyl, alkoxy or hydroxy;
R$^2$ is

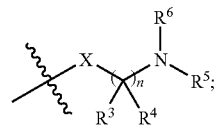

X is —O— or —NR$^7$—;
n is 2 or 3;
R$^3$ and R$^4$ each independently is hydrogen or alkyl, or R$^3$ and R$^4$ together may form a —C(O)—;
R$^5$ and R$^6$ each independently is hydrogen or alkyl, or R$^5$ and R$^6$ together with the nitrogen to which they are attached may form a five- or six-membered ring that optionally includes an additional heteroatom selected from O, N and S, or one of R$^5$ and R$^6$ and one of R$^3$ and R$^4$ together with the atoms to which they are attached may form a five- or six-membered ring that optionally includes an additional heteroatom selected from O, N and S; and
R$^7$ is hydrogen or alkyl.

2. The compound of claim 1, wherein p is 1 or 2.
3. The compound of claim 2, wherein q is 2.
4. The compound of claim 3, wherein Ar is optionally substituted phenyl.
5. The compound of claim 4, wherein m is 0 or 1.
6. The compound of claim 5, wherein n is 2.
7. The compound of claim 6, wherein X is —O—.
8. The compound of claim 7, wherein R$^3$ and R$^4$ are hydrogen.
9. The compound of claim 8, wherein R$^5$ and R$^6$ are hydrogen.
10. The compound of claim 8, wherein one of R$^5$ and R$^6$ is hydrogen and the other is alkyl.
11. The compound of claim 6, wherein X is —NR$^7$—.
12. The compound of claim 11, wherein R$^3$ and R$^4$ are hydrogen.
13. The compound of claim 12, wherein R$^5$ and R$^6$ are hydrogen.

14. The compound of claim 12, wherein one of $R^5$ and $R^6$ is hydrogen and the other is alkyl.

15. The compound of claim 5, wherein n is 3.

16. The compound of claim 15, wherein X is —O—.

17. The compound of claim 16, wherein one of $R^5$ and $R^6$ and one of $R^3$ and $R^4$ together with the atoms to which they are attached form a six membered ring.

18. The compound of claim 15, wherein X is —$NR^7$—.

19. The compound of claim 18, wherein one of $R^5$ and $R^6$ and one of $R^3$ and $R^4$ together with the atoms to which they are attached form a six membered ring.

20. The compound of claim 1, wherein $R^2$ is aminoalkoxyalkyl.

21. The compound of claim 1, wherein $R^2$ is:

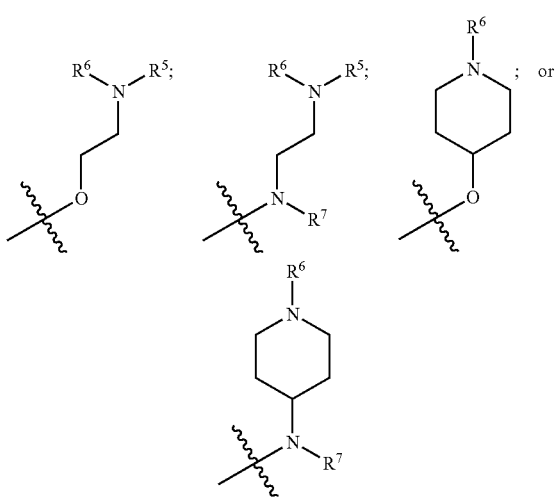

wherein $R^5$, $R^6$ and $R^7$ are as recited in claim 1.

22. The compound of claim 1, wherein said compound is of formula II:

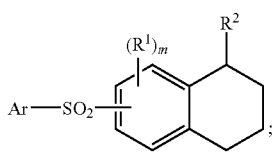

and wherein m, Ar, $R^1$ and $R^2$ are as recited in claim 1.

23. The compound of claim 1, wherein said compound is of formula IIIa or IIIb:

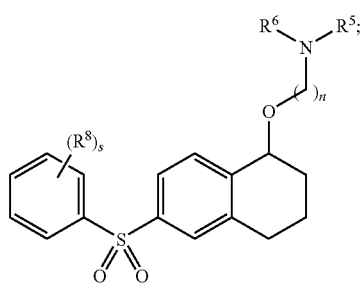

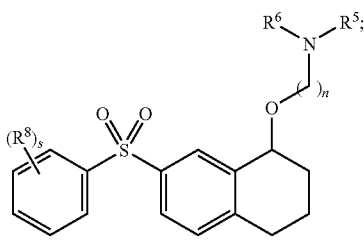

wherein:

s is from 0 to 4;

each $R^8$ is independently halo, alkyl, alkoxy, haloalkyl, heteroalkyl, cyano, —S(O)$_t$—$R^a$, —C(=O)—$NR^bR^c$, —SO$_2$—$NR^bR^c$, —N($R^d$)—C(=O)—$R^e$, or —C(=O) $R^e$, where r is from 0 to 2, $R^a$, $R^b$, $R^c$ and $R^d$ each independently is hydrogen or alkyl, and $R^e$ is hydrogen, alkyl, alkoxy or hydroxy; and n, $R^5$ and $R^6$ are as recited in claim 1.

24. The compound of claim 23, wherein s is from 0 to 2, and each $R^8$ is independently halo, alkyl, alkoxy, or haloalkyl.

25. The compound of claim 24, wherein n is 2.

26. The compound of claim 25, wherein said compound is of the formula IIIa.

27. The compound of claim 26, wherein $R^5$ is hydrogen and $R^6$ is methyl.

28. The compound of claim 1, wherein said compound is selected from:

N-(2-Amino-ethyl)-2-(5-benzenesulfonyl-indan-1-yloxy)-acetamide;

2-(5-Benzenesulfonyl-indan-1-yloxy)-ethylamine;

{2-[5-(2-Fluoro-benzenesulfonyl)-indan-1-yloxy]-ethyl}-methyl-amine;

(5-Benzenesulfonyl-indan-1-yl)-piperidin-4-yl-amine;

[2-(6-Benzenesulfonyl-1,2,3,4-tetrahydro-naphthalen-1-yloxy)-ethyl]-methyl-amine;

[2-(7-Benzenesulfonyl-1,2,3,4-tetrahydro-naphthalen-1-yloxy)-ethyl]-methyl-amine;

(6-Benzenesulfonyl-1,2,3,4-tetrahydro-naphthalen-1-yl)-piperidin-4-yl-amine;

N-(6-Benzenesulfonyl-1,2,3,4-tetrahydro-naphthalen-1-yl)-N'-methyl-ethane-1,2-diamine;

N'-(6-Benzenesulfonyl-1,2,3,4-tetrahydro-naphthalen-1-yl)-N,N-dimethyl-ethane-1,2-diamine; and N-(6-Benzenesulfonyl-1,2,3,4-tetrahydro-naphthalen-1-yl)-N,N'-dimethyl-ethane-1,2-diamine.

29. A pharmaceutical composition comprising an effective amount of the compound of claim 1 in admixture with a pharmaceutically acceptable carrier.

30. A method for treating psychoses, schizophrenia or manic depressions, said method comprising administering to said subject a therapeutically effective amount of a compound of claim 1.

* * * * *